United States Patent
Engman et al.

(10) Patent No.: US 11,040,214 B2
(45) Date of Patent: Jun. 22, 2021

(54) WEARABLE CARDIOVERTER DEFIBRILLATOR (WCD) SYSTEM HAVING MAIN UI THAT CONVEYS MESSAGE AND PERIPHERAL DEVICE THAT AMPLIFIES THE MESSAGE

(71) Applicant: West Affum Holdings Corp., Grand Cayman (KY)

(72) Inventors: Zoie Engman, Kirkland, WA (US); Aaron Piazza, Lake Forest Park, WA (US); Christoffer Peter Hart Hansen, Seattle, WA (US); David P. Finch, Bothell, WA (US); Laura M. Gustavson, Redmond, WA (US); Erik L. Schneider, Kirkland, WA (US); Erick Roane, Bellevue, WA (US); Amanda K. Hall, Seattle, WA (US)

(73) Assignee: West Affum Holdings Corp., Grand Cayman (KY)

( * ) Notice: Subject to any disclaimer, the term of this patent is extended or adjusted under 35 U.S.C. 154(b) by 188 days.

(21) Appl. No.: 16/283,342

(22) Filed: Feb. 22, 2019

(65) Prior Publication Data
US 2019/0269930 A1 Sep. 5, 2019

Related U.S. Application Data

(60) Provisional application No. 62/637,296, filed on Mar. 1, 2018.

(51) Int. Cl.
*A61N 1/39* (2006.01)
*A61N 1/04* (2006.01)
(Continued)

(52) U.S. Cl.
CPC .......... *A61N 1/3993* (2013.01); *A61B 5/0205* (2013.01); *A61B 5/6804* (2013.01);
(Continued)

(58) Field of Classification Search
CPC .. A61N 1/3993; A61N 1/3968; A61N 1/3904; A61N 1/046; A61N 1/0484;
(Continued)

(56) References Cited

U.S. PATENT DOCUMENTS

| 3,724,355 A | 4/1973 | Unger |
| 4,583,524 A | 4/1986 | Hutchins |

(Continued)

FOREIGN PATENT DOCUMENTS

| WO | 1198039061 A2 | 9/1998 |
| WO | 1998039061 A2 | 9/1998 |
| WO | 2012064604 A1 | 5/2012 |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Jounal, May 31, 2013, pp. 1-14, doi:10.1093/eurheartj/eht167, European Society of Cardiology.

(Continued)

*Primary Examiner* — Amanda K Hulbert
*Assistant Examiner* — Philip C Edwards
(74) *Attorney, Agent, or Firm* — Christensen O'Connor Johnson K

(57) ABSTRACT

In embodiments, a Wearable Cardiac Defibrillator (WCD) system is configured to be worn by an ambulatory patient. The WCD system includes a main user interface (UI) output device that can output an image, sound or vibration as a main message about a condition of the patient or the WCD system. The patient may further carry a peripheral device that can also output an image, sound or vibration as a peripheral message about the condition. The peripheral message may mirror the main message at least in part, amplify it, and so on. The availability of the peripheral message provides the (Continued)

patient with the opportunity to better perceive the main message, and the flexibility to receive and react to it discreetly, learn more about the condition, and so on.

25 Claims, 9 Drawing Sheets

(51) Int. Cl.
G06F 3/14 (2006.01)
A61B 5/00 (2006.01)
A61B 5/0205 (2006.01)
G08B 3/10 (2006.01)
G08B 6/00 (2006.01)
A61B 5/024 (2006.01)
A61B 7/04 (2006.01)
A61B 5/08 (2006.01)
A61B 5/029 (2006.01)
A61B 5/1455 (2006.01)
A61B 5/11 (2006.01)
A61B 7/00 (2006.01)
A61B 5/026 (2006.01)
A61B 5/363 (2021.01)

(52) U.S. Cl.
CPC ........... A61N 1/046 (2013.01); A61N 1/0484 (2013.01); A61N 1/3904 (2017.08); A61N 1/3968 (2013.01); A61N 1/3975 (2013.01); G06F 3/1454 (2013.01); A61B 5/0002 (2013.01); A61B 5/024 (2013.01); A61B 5/026 (2013.01); A61B 5/029 (2013.01); A61B 5/0816 (2013.01); A61B 5/11 (2013.01); A61B 5/1455 (2013.01); A61B 5/363 (2021.01); A61B 5/7275 (2013.01); A61B 7/003 (2013.01); A61B 7/04 (2013.01); G08B 3/10 (2013.01); G08B 6/00 (2013.01)

(58) Field of Classification Search
CPC .. A61N 1/3975; A61B 5/6804; A61B 5/0205; A61B 5/024; A61B 7/04; A61B 5/0816; A61B 5/029; A61B 5/0464; A61B 5/1455; A61B 5/7275; A61B 5/11; A61B 5/0002; A61B 7/003; A61B 5/026; G06F 3/1454; G08B 3/10; G08B 6/00
USPC .......................................................... 607/7
See application file for complete search history.

(56) References Cited

U.S. PATENT DOCUMENTS

| | | | |
|---|---|---|---|
| 4,619,265 A | 10/1986 | Morgan et al. |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,353,793 A | 10/1994 | Bornn |
| RE34,800 E | 11/1994 | Hutchins |
| 5,394,892 A | 3/1995 | Kenny |
| 5,405,362 A | 4/1995 | Kramer et al. |
| 5,474,574 A | 12/1995 | Payne et al. |
| 5,662,690 A | 9/1997 | Cole et al. |
| 5,782,878 A | 7/1998 | Morgan et al. |
| 5,792,204 A | 8/1998 | Snell |
| 5,902,249 A | 5/1999 | Lysler |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,437,083 B1 | 7/2002 | Owen et al. |
| 6,529,875 B1 | 3/2003 | Nakajima |
| 6,546,285 B1 | 4/2003 | Owen et al. |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,644,925 B2 | 2/2014 | Volpe et al. |
| 8,676,313 B2 | 3/2014 | Volpe et al. |
| 8,897,860 B2 | 11/2014 | Volpe et al. |
| 8,965,500 B2 | 2/2015 | Macho et al. |
| 9,008,801 B2 | 4/2015 | Kaib et al. |
| 9,131,901 B2 | 9/2015 | Volpe et al. |
| 9,132,267 B2 | 9/2015 | Kaib |
| 9,345,898 B2 | 5/2016 | Piha et al. |
| 9,408,548 B2 | 8/2016 | Volpe et al. |
| 9,757,576 B2 | 9/2017 | Sullivan et al. |
| 9,878,171 B2 | 1/2018 | Kaib |
| 9,901,741 B2 | 2/2018 | Chapman et al. |
| 10,016,613 B2 | 7/2018 | Kavounas |
| 10,617,881 B2 * | 4/2020 | Pavel .................. A61N 1/3987 |
| 2002/0181680 A1 | 12/2002 | Linder et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0265265 A1 | 10/2012 | Razavi et al. |
| 2012/0283794 A1 | 11/2012 | Kaib et al. |
| 2012/0302860 A1 | 11/2012 | Volpe et al. |
| 2013/0041243 A1 | 2/2013 | Byrd et al. |
| 2013/0085538 A1 | 4/2013 | Volpe et al. |
| 2013/0144355 A1 | 6/2013 | Macho et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0046391 A1 | 2/2014 | Cowan et al. |
| 2014/0070957 A1 | 3/2014 | Longinotti-Buritonil et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0331996 A1 * | 11/2015 | Gustavson ......... A61N 1/37211 705/3 |
| 2016/0004831 A1 | 1/2016 | Carlson et al. |
| 2016/0212103 A1 | 7/2016 | Rhoads et al. |
| 2016/0283900 A1 | 9/2016 | Johnson et al. |
| 2016/0286584 A1 | 9/2016 | Lee |
| 2017/0017454 A1 | 1/2017 | Kim et al. |
| 2017/0182330 A1 * | 6/2017 | Schneider ............ A61N 1/3968 |
| 2017/0319862 A1 | 11/2017 | Foshee, Jr. et al. |
| 2017/0367591 A1 | 12/2017 | Jorgenseon |

(56) References Cited

U.S. PATENT DOCUMENTS

| | | |
|---|---|---|
| 2018/0184933 A1 | 7/2018 | Sullivan et al. |
| 2018/0185662 A1 | 7/2018 | Foshee, Jr. et al. |
| 2018/0243578 A1 | 8/2018 | Volosin |
| 2018/0275836 A1 | 9/2018 | Hermans et al. |
| 2018/0324486 A1 | 11/2018 | Lee et al. |
| 2019/0030350 A1* | 1/2019 | Finch .................. A61N 1/3904 |
| 2019/0030352 A1 | 1/2019 | Sullivan et al. |
| 2019/0076666 A1 | 3/2019 | Medema |

OTHER PUBLICATIONS

Lifecor LifeVest System Model WCD 3100 Operator's Manual, 2006, PN 20B0040 Rev FI, Zoll Lifecor Corporation, Pittsburgh, PA.

Heartstart MRx and XL AED Algorithm—Application Note, Jul. 2001, Edition 2 Phillips Healthcare, USA.

ZOLL LifeVest Model 4000 Patient Manual PN 20B0047 Rev B, (C) 2009-2012.

Office Action issued in corresponding Japanese Patent Application No. 2019-035091, filed Feb. 28, 2019, 5 pages.

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

\* cited by examiner

SAMPLE COMPONENTS OF EXTERNAL DEFIBRILLATOR

COMPONENTS OF SAMPLE WCD SYSTEM WITH PERIPHERAL DEVICE

PATIENT OPTIONS

WEARABLE CARDIOVERTER DEFIBRILLATOR (WCD) SYSTEM HAVING MAIN UI THAT CONVEYS MESSAGE AND PERIPHERAL DEVICE THAT AMPLIFIES THE MESSAGE

CROSS REFERENCE TO RELATED PATENT APPLICATIONS

This patent application claims priority from U.S. Provisional Patent Application Ser. No. 62/637,296, filed on Mar. 1, 2018.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim. Some observers have thought that SCA is the same as a heart attack, which it is not.

Some people have an increased risk of SCA. Such people include patients who have had a heart attack, or a prior SCA episode. A frequent recommendation for these people is to receive an Implantable Cardioverter Defibrillator (ICD). The ICD is surgically implanted in the chest, and continuously monitors the patient's electrocardiogram (ECG). If certain types of heart arrhythmias are detected, then the ICD delivers an electric shock through the heart.

As a further precaution, people who have been identified to have an increased risk of an SCA are sometimes given a Wearable Cardioverter Defibrillator (WCD) system, to wear until the time that their ICD is implanted. Early versions of such systems were called wearable cardiac defibrillator systems. A WCD system typically includes a harness, vest, belt, or other garment that the patient is to wear. The WCD system further includes electronic components, such as a defibrillator and electrodes, coupled to the harness, vest, or other garment. When the patient wears the WCD system, the electrodes may make good electrical contact with the patient's skin, and therefore can help sense the patient's ECG. If a shockable heart arrhythmia is detected from the ECG, then the defibrillator delivers an appropriate electric shock through the patient's body, and thus through the heart. This may restart the patient's heart and thus save their life.

All subject matter discussed in this Background section of this document is not necessarily prior art, and may not be presumed to be prior art simply because it is presented in this Background section. Plus, any reference to any prior art in this description is not, and should not be taken as, an acknowledgement or any form of suggestion that such prior art forms parts of the common general knowledge in any art in any country. Along these lines, any recognition of problems in the prior art discussed in this Background section or associated with such subject matter should not be treated as prior art, unless expressly stated to be prior art. Rather, the discussion of any subject matter in this Background section should be treated as part of the approach taken towards the particular problem by the inventors. This approach in and of itself may also be inventive.

BRIEF SUMMARY

The present description gives instances of wearable cardioverter defibrillator (WCD) systems, components of such systems, storage media that may store programs, and methods, the use of which may help overcome problems and limitations of the prior art.

In embodiments, a Wearable Cardiac Defibrillator (WCD) system is configured to be worn by an ambulatory patient. The WCD system includes a main user interface (UI) output device that can output an image, sound or vibration as a main message about a condition of the patient or the WCD system. The patient may further carry a peripheral device that can also output an image, sound or vibration as a peripheral message about the condition. The peripheral message may mirror the main message at least in part, amplify it, and so on. The availability of the peripheral message provides the patient with the opportunity to better perceive the main message, and the flexibility to receive and react to it discreetly, learn more about the condition, and so on.

These and other features and advantages of the claimed invention will become more readily apparent in view of the embodiments described and illustrated in this specification, namely in this written specification and the associated drawings.

DETAILED DESCRIPTION

As has been mentioned, the present description is about wearable cardioverter defibrillator (WCD) systems, components of such systems, storage media that may store programs, and methods. Embodiments are now described in more detail.

A wearable cardioverter defibrillator (WCD) system according to embodiments may protect an ambulatory patient by electrically restarting their heart if needed. Such a WCD system may have a number of components. These components can be provided separately as modules that can be interconnected, or can be combined with other components, and so on.

Figure 1:
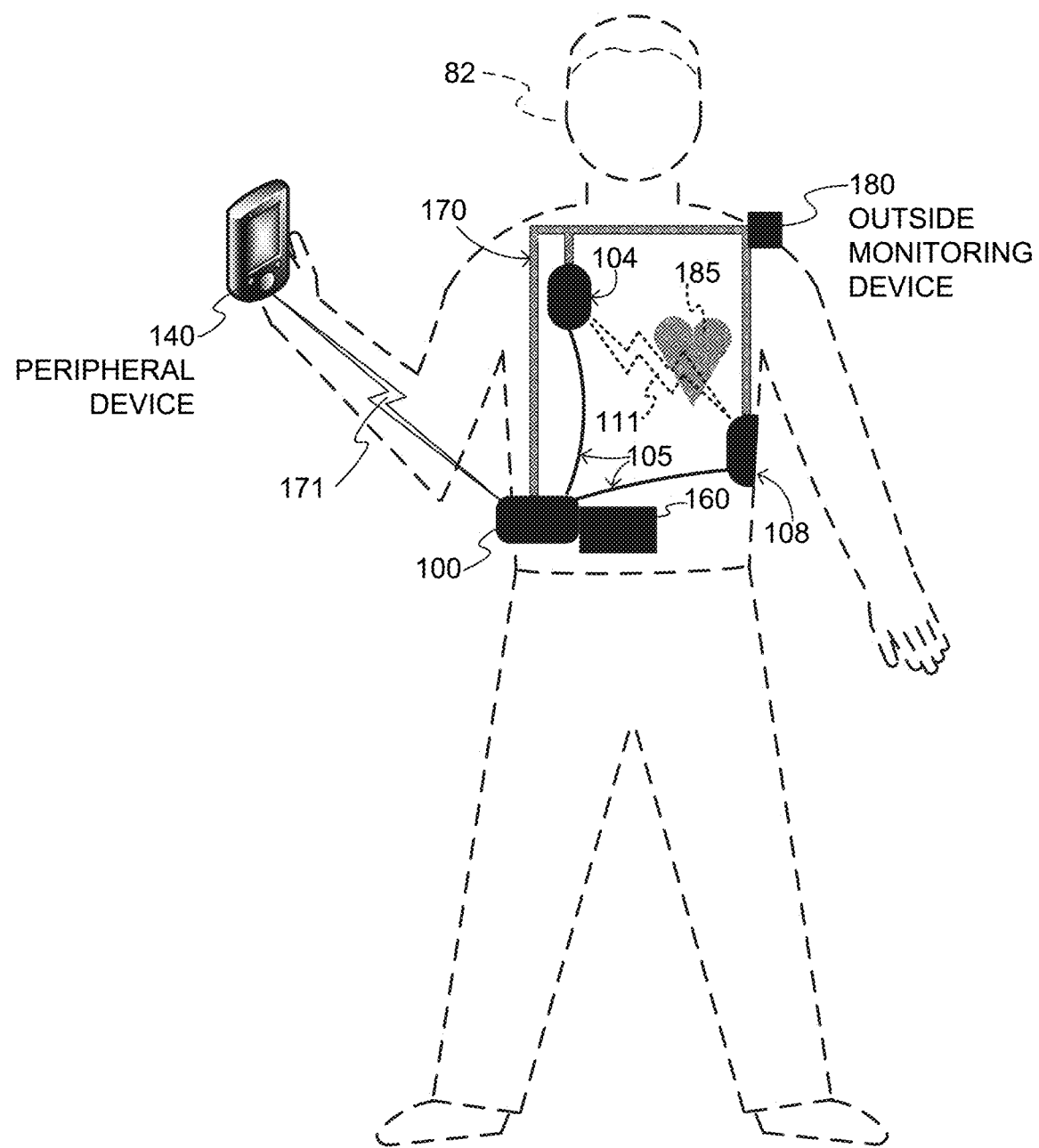
FIG. 1 is a diagram of components of a sample wearable cardioverter defibrillator (WCD) system, made according to embodiments.

FIG. 1 depicts a patient 82. Patient 82 may also be referred to as a person and/or wearer, since the patient is wearing components of the WCD system. Patient 82 is ambulatory, which means that, while wearing the wearable portion of the WCD system, patient 82 can walk around and is not necessarily bed-ridden. While patient 82 may be considered to be also a "user" of the WCD system, this is not a requirement. For instance, a user of the wearable cardioverter defibrillator (WCD) may also be a clinician such as a doctor, nurse, emergency medical technician (EMT) or other similarly tasked individual or group of individuals. In some cases, a user may even be a bystander. The particular context of these and other related terms within this description should be interpreted accordingly.

A WCD system according to embodiments can be configured to defibrillate the patient who is wearing the designated parts the WCD system. Defibrillating can be by the WCD system delivering an electrical charge to the patient's body in the form of an electric shock. The electric shock can be delivered in one or more pulses.

In particular, FIG. 1 also depicts components of a WCD system made according to embodiments. One such component is a support structure 170 that is wearable by ambulatory patient 82. Accordingly, support structure 170 is configured to be worn by ambulatory patient 82 for at least several hours per day, and for at least several days, even a few months. It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to analogous articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient's body by adhesive material, for example as shown and described in U.S. Pat. No. 8,024,037. Support structure 170 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples.

FIG. 1 shows a sample external defibrillator 100. As described in more detail later in this document, some aspects of external defibrillator 100 include a housing and an energy storage module within the housing. As such, in the context of a WCD system, defibrillator 100 is sometimes called a main electronics module. The energy storage module can be configured to store an electrical charge. Other components can cause at least some of the stored electrical charge to be discharged via electrodes through the patient, so as to deliver one or more defibrillation shocks through the patient.

FIG. 1 also shows sample defibrillation electrodes 104, 108, which are coupled to external defibrillator 100 via electrode leads 105. Defibrillation electrodes 104, 108 can be configured to be worn by patient 82 in a number of ways. For instance, defibrillator 100 and defibrillation electrodes 104, 108 can be coupled to support structure 170, directly or indirectly. In other words, support structure 170 can be configured to be worn by ambulatory patient 82 so as to maintain at least one of electrodes 104, 108 on the body of ambulatory patient 82, while patient 82 is moving around, etc. The electrode can be thus maintained on the body by being attached to the skin of patient 82, simply pressed against the skin directly or through garments, etc. In some embodiments the electrode is not necessarily pressed against the skin, but becomes biased that way upon sensing a condition that could merit intervention by the WCD system. In addition, many of the components of defibrillator 100 can be considered coupled to support structure 170 directly, or indirectly via at least one of defibrillation electrodes 104, 108.

When defibrillation electrodes 104, 108 make good electrical contact with the body of patient 82, defibrillator 100 can administer, via electrodes 104, 108, a brief, strong electric pulse 111 through the body. Pulse 111 is also known as shock, defibrillation shock, therapy, electrotherapy, therapy shock, etc. Pulse 111 is intended to go through and restart heart 85, in an effort to save the life of patient 82. Pulse 111 can further include one or more pacing pulses of lesser magnitude to simply pace heart 85 if needed, and so on.

A prior art defibrillator typically decides whether to defibrillate or not based on an ECG signal of the patient. However, external defibrillator 100 may initiate defibrillation, or hold-off defibrillation, based on a variety of inputs, with the ECG signal merely being one of these inputs.

A WCD system according to embodiments can obtain data from patient 82. For collecting such data, the WCD system may optionally include at least an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document.

For some of these parameters, device 180 may include one or more sensors or transducers. Each one of such sensors can be configured to sense a parameter of patient 82, and to render an input responsive to the sensed parameter. In some embodiments the input is quantitative, such as values of a sensed parameter; in other embodiments the input is qualitative, such as informing whether or not a threshold is crossed, and so on. Sometimes these inputs about patient 82 are also called physiological inputs and patient inputs. In embodiments, a sensor can be construed more broadly, as encompassing many individual sensors.

Optionally, device 180 is physically coupled to support structure 170. In addition, device 180 may be communicatively coupled with other components that are coupled to support structure 170. Such communication can be implemented by a communication module, as will be deemed applicable by a person skilled in the art in view of this description.

In embodiments, one or more of the components of the shown WCD system may be customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. The measured values of such baseline physiological parameters can be used to customize the WCD system, in order to make its diagnoses more accurate, since patients' bodies differ from one another. Of course, such parameter values can be stored in a memory of the WCD system, and so on. Moreover, a programming interface can be made according to embodiments, which receives such measured values of baseline physiological parameters. Such a programming interface may input automatically in the WCD system these, along with other data.

The components of the WCD system of FIG. 1 also include a communication unit 160. Communication unit 160 can be a device for patient 82 to exchange information with the WCD system. In particular, communication unit 160 may have a user interface that is configured to enable patient 82 to read messages of the WCD system, and maybe enter user inputs.

In some embodiments, communication unit 160 is integrated with defibrillator 100. As such, they can have the same housing, the same processors, and so on. If communication unit 160 is provided as a separate unit from defibrillator 100, it can be configured to be coupled to support structure 170, and electrically coupled with defibrillator 100 via a cable, which can be a permanent cable or a USB or Firewire connection.

For use, patient 82 may reach into their clothes to access communication unit 160. In embodiments where a cable is used, patient 82 may bring communication unit 160 to a comfortable position for reading the system messages. A problem with this arrangement, however, is that other people who see communication unit 160 might become curious, or even apprehensive. According to embodiments, some of the WCD system messages are also conveyed via a peripheral device 140, redundantly with unit 160 or not. Peripheral device 140 can be configured to be carried by ambulatory patient 82, for example by being implemented as a mobile communication device, e.g. a cellphone, a computer tablet, etc.

In embodiments, then, patient 82 carries peripheral device 140 on their person for typically much of the day. Patient 82 may carry device 140 in a pocket, in a special holder, or even wear it on their wrist. Patient 82 may use device 140 to communicate with the WCD system, which is why patient 82 may also be referred to as user 82. Peripheral device 140 has a peripheral UI output device, which can be implemented in number of ways. For example, the peripheral UI output device can include a peripheral speaker configured to emit a sound, a peripheral vibration device configured to generate a vibration, a peripheral screen configured to display an image, and so on. The peripheral screen can be a touchscreen. As such, a certain type of UI output device will output a corresponding human-perceptible indication (HPI), such as an image, a light lighting, a sound, a vibration, etc. Peripheral device 140 can be configured to further enable patient 82 to enter inputs that in this document are often called wireless inputs. Wireless communication links may be established and used in embodiments, for exchanging data, voice, etc.

A peripheral device such as device 140 can be a custom-made device that is part of the WCD system. If made to look substantially like a common, commercially available mobile communication device, it might help preserve the privacy of patient 82 as to the fact that he or she is wearing a medical device, and thus also help preserve their dignity. In making such a custom-made device 140 appear like a commercially available mobile communication device, care should be taken to not use others' intellectual property rights without their permission.

Alternately, peripheral device 140 can be a wireless telephone, a smartphone, a Personal Digital Assistant (PDA), a personal electronic device, a pager, a laptop computer, a tablet, an e-reader, and so on. It can store and run a software application, also known as app, made according to embodiments, so as to perform various functions as described. In such embodiments, peripheral device 140 can communicate with a wireless service provider network (not shown) via a remote comlink (not shown). For purposes of this document, "comlink" means a communication link, and a "remote comlink" means a wireless comlink established between devices that are at least 500 feet (150 m) away from each other, and typically farther, such as a cellular communication link. In such instances, the remote comlink can be used for a number of other functions, such as dialing an emergency number (e.g. 911 in the US), which may also be accessible via the mobile communication device directly. In addition, the location of the patient may be determined by GPS. If the WCD system and the communication device have been paired and one of them knows that it is physically close to the other, GPS information may thus become known and communicated to EMS services. The communication device may provide a redundant communication path for the data of the WCD system. This redundant communication path might be used as a secondary communication path for remote monitoring data if a primary, in-house internet path is not available for the WCD system to report. The remote comlink can also be used by a remote caregiver to provide patient 82 with troubleshooting assistance, motivational feedback, etc.

Peripheral device 140 can thus be configured to establish a local comlink 171 with the communication module of the WCD system, which may be inside the same module as defibrillator 100. If peripheral device 140 is indeed a wireless telephone or other independent standalone communication device, a local comlink may be established first pursuant to some authentication. Local comlink 171 may be established by the initiative of peripheral device 140, the communication module, or both. For purposes of this document, a "local comlink" means a wireless communication link established between devices that are at most 50 feet (15 m) away from each other, and typically closer, such as when patient 82 is holding device 140. Local comlink 171 can be a wireless link. Data may be exchanged via local comlink 171, in either direction, or in both directions. In embodiments, local comlink 171 uses radio transmission technology that can be broadband and/or shortwave. Local comlink 171 may use Bluetooth technology, Wi-Fi technology, Zigbee or other suitable short-range wireless technology.

Figure 2:
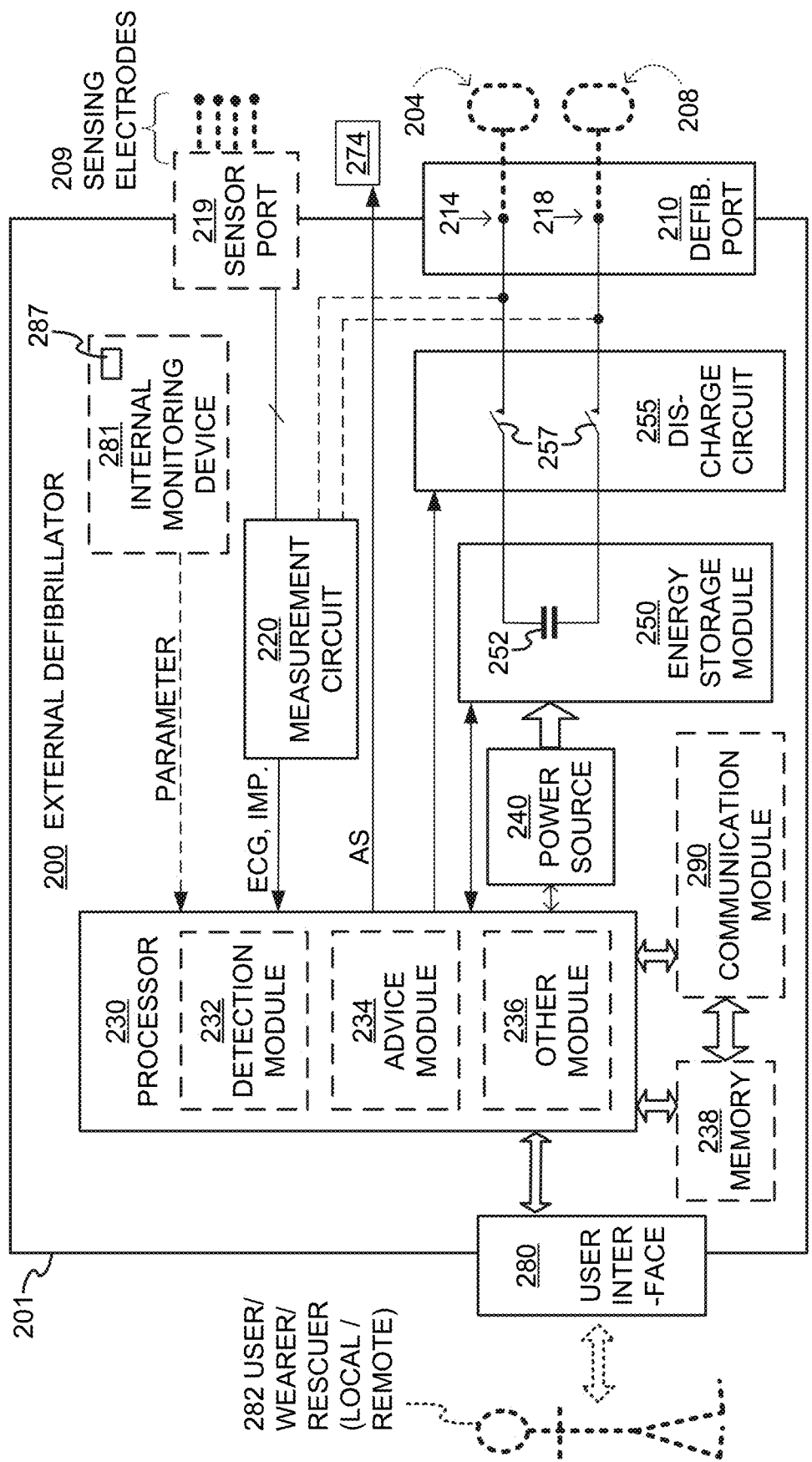
FIG. 2 is a diagram showing sample components of an external defibrillator, such as the one belonging in the system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as ambulatory patient 82 of FIG. 1. Defibrillator 200 may further include a user interface (UI) 280, or such a UI 280 can be part of communication unit 160. UI 280 may be for a user 282.

User 282 can be patient 82, also known as wearer 82. Or, user 282 can be a local rescuer at the scene, such as a bystander who might offer assistance, or a trained person. Or, user 282 might be a remotely located trained caregiver in communication with the WCD system.

User interface 280, which can be implemented by communication unit 160, can be made in a number of ways. User interface 280 may include output devices, which can be visual, audible or tactile, for communicating to a user by outputting images, sounds or vibrations. Images, sounds, vibrations, and anything that can be perceived by user 282 can also be called human-perceptible indications (HPIs). There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds and/or words to warn bystanders, etc.

User interface 280 may further include input devices for receiving inputs from users. Such input devices may include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 may include one or more sensors, as also described elsewhere in this document.

Patient parameters may include patient physiological parameters. Patient physiological parameters may include, for example and without limitation, those physiological parameters that can be of any help in detecting by the WCD system whether or not the patient is in need of a shock or other intervention or assistance. Patient physiological parameters may also optionally include the patient's medical history, event history and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an $SpO_2$ sensor, and so on. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection.

In some embodiments, the local parameter is a trend that can be detected in a monitored physiological parameter of patient 282. A trend can be detected by comparing values of parameters at different times over short and long terms. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$, $CO_2$, or other parameters such as those mentioned above, f) respiratory function, respiratory rate, etc.; g) motion, level of activity; and so on. Once a trend is detected, it can be stored and/or reported via a communication link, along perhaps with a warning if warranted. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may thus include a motion detector. In embodiments, a motion detector can be implemented within monitoring device 180 or monitoring device 281. Such a motion detector can be made in many ways as is known in the art, for example by using an accelerometer. In this example, a motion detector 287 is implemented within monitoring device 281. A motion detector of a WCD system according to embodiments can be configured to detect a motion event. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed, if monitoring device 180 or 281 includes a GPS location sensor as per the above, and if it is presumed that the patient is wearing the WCD system.

Defibrillator 200 typically includes a defibrillation port 210, which can be a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer at least some of the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, e.g. a 12-lead signal, or a signal from a different number of leads, especially if they make good electrical contact with the body of the patient and in particular with the skin of the patient. As with defibrillation electrodes 204, 208, the support structure can be configured to be worn by patient 282 so as to maintain sensing electrodes 209 on a body of patient 282. For example, sensing electrodes 209 can be attached to the inside of support structure 170 for making good electrical contact with the patient, similarly with defibrillation electrodes 204, 208.

Optionally a WCD system according to embodiments also includes a fluid that it can deploy automatically between the electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel, so that it does not flow away, after being deployed, from the location it is released near the electrode. The fluid can be used for both defibrillation electrodes 204, 208, and for sensing electrodes 209.

The fluid may be initially stored in a fluid reservoir, not shown in FIG. 2. Such a fluid reservoir can be coupled to the support structure. In addition, a WCD system according to embodiments further includes a fluid deploying mechanism 274. Fluid deploying mechanism 274 can be configured to cause at least some of the fluid to be released from the reservoir, and be deployed near one or both of the patient locations to which electrodes 204, 208 are configured to be attached to the patient. In some embodiments, fluid deploying mechanism 274 is activated prior to the electrical discharge responsive to receiving activation signal AS from a processor 230, which is described more fully later in this document.

In some embodiments, defibrillator 200 also includes a measurement circuit 220, as one or more of its modules working together with its sensors or transducers. Measurement circuit 220 senses one or more electrical physiological signals of the patient from sensor port 219, if provided. Even if defibrillator 200 lacks sensor port 219, measurement circuit 220 may optionally obtain physiological signals through nodes 214, 218 instead, when defibrillation electrodes 204, 208 are attached to the patient. In these cases, the input reflects an ECG measurement. The patient parameter can be an ECG, which can be sensed as a voltage difference between electrodes 204, 208. In addition, the patient parameter can be an impedance, which can be sensed between electrodes 204, 208 and/or between the connections of sensor port 219 considered pairwise. Sensing the impedance can be useful for detecting, among other things, whether these electrodes 204, 208 and/or sensing electrodes 209 are not making good electrical contact with the patient's body. These patient physiological signals may be sensed when available. Measurement circuit 220 can then render or generate information about them as inputs, data, other signals, etc. As such, measurement circuit 220 can be configured to render a patient input responsive to a patient parameter sensed by a sensor. In some embodiments, measurement circuit 220 can be configured to render a patient input, such as values of an ECG signal, responsive to the ECG signal sensed by sensing electrodes 209. More strictly speaking, the information rendered by measurement circuit 220 is output from it, but this information can be called an input because it is received as an input by a subsequent device or functionality.

Defibrillator 200 also includes a processor 230. Processor 230 may be implemented in a number of ways. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAA5), Programmable Logic Devices (PLDs), Application Specific Integrated Circuits (ASICs), any combination of one or more of these, and so on.

Processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as inputs, data that reflect values, or values of other signals, may be used by the VF detector to determine whether the patient is experiencing VF. Detecting VF is useful, because VF typically results in SCA. Detection module 232 can also include a Ventricular Tachycardia (VT) detector for detecting VT, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments, and determine whether or not a shock criterion is met. The determination can be made from a rhythm analysis of the captured ECG signal or otherwise. For example, there can be shock decisions for VF, VT, etc.

In some embodiments, when the determination is to shock, an electrical charge is delivered to the patient. Delivering the electrical charge is also known as discharging and shocking the patient. As mentioned above, such can be for defibrillation, pacing, and so on.

In perfect conditions, a very reliable shock/no shock determination can be made from a segment of the sensed ECG signal of the patient. In practice, however, the ECG signal is often corrupted by electrical noise, which makes it difficult to analyze. Too much noise sometimes causes an incorrect detection of a heart arrhythmia, resulting in a false alarm to the patient. Noisy ECG signals may be handled as described in U.S. patent application Ser. No. 16/037,990, filed on Jul. 17, 2018 and since published as US 2019/0030351 A1, and also in U.S. patent application Ser. No. 16/038,007, filed on Jul. 17, 2018 and since published as U.S. 2019/0030352 A1, both by the same applicant and incorporated herein by reference.

Processor 230 can include additional modules, such as other module 236, for other functions. In addition, if internal monitoring device 281 is indeed provided, processor 230 may receive its inputs, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or be stored there after it is received by defibrillator 200.

Defibrillator 200 can optionally include a communication module 290. In some embodiments, communication module 290 is implemented in separate communication unit 160. Communication module 290 may be configured to establish one or more wired or wireless communication links with other devices of other entities, such as a remote assistance center, Emergency Medical Services (EMS), and so on. The communication links can be used to transfer data and commands. The data may be patient data, event information, therapy attempted, CPR performance, system data, environmental data, and so on. For example, communication module 290 may transmit wirelessly, e.g. on a daily basis, heart rate, respiratory rate, and other vital signs data to a server accessible over the internet, for instance as described in US 20140043149. This data can be analyzed directly by the patient's physician and can also be analyzed automatically by algorithms designed to detect a developing illness and then notify medical personnel via text, email, phone, etc. Module 290 may also include such interconnected subcomponents as may be deemed necessary by a person skilled in the art, for example an antenna, portions of a processor, supporting electronics, outlet for a telephone or a network cable, etc.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy-storing capacitor, and so on. Appropriate components may be included to provide for charging or replacing power source 240. In some embodiments, power source 240 is controlled and/or monitored by processor 230.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

A decision to shock can be made responsive to the shock criterion being met, as per the above-mentioned determination. When the decision is to shock, processor 230 can be configured to cause at least some or all of the electrical charge stored in module 250 to be discharged through patient 82 while the support structure is worn by patient 82, so as to deliver a shock 111 to patient 82.

For causing the discharge, defibrillator 200 moreover includes a discharge circuit 255. When the decision is to shock, processor 230 can be configured to control discharge circuit 255 to discharge through the patient at least some of all of the electrical charge stored in energy storage module 250. Discharging can be to nodes 214, 218, and from there to defibrillation electrodes 204, 208, so as to cause a shock to be delivered to the patient. Circuit 255 can include one or more switches 257. Switches 257 can be made in a number of ways, such as by an H-bridge, and so on. Circuit 255 could also be thus controlled via processor 230, and/or user interface 280.

Defibrillator 200 can optionally include other components.

Figure 3:
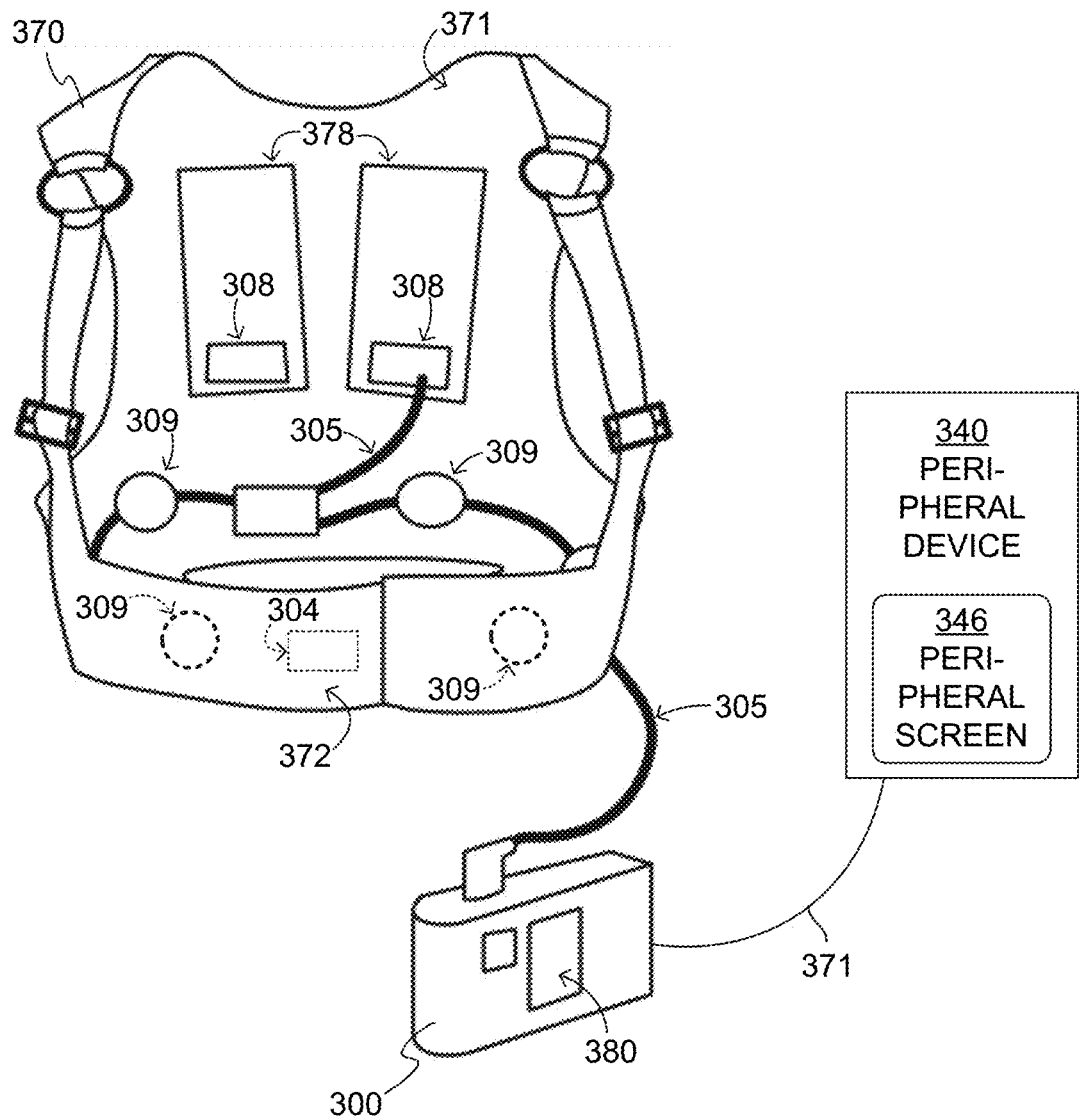
FIG. 3 is a diagram of sample embodiments of components of a WCD system.

FIG. 3 is a diagram of sample embodiments of components of an WCD system. A support structure 370 includes a vest-like wearable garment. Support structure 370 has a back side 371, and a front side 372 that closes in front of the chest of the patient.

The WCD system of FIG. 3 also includes an external defibrillator 300. In this example, there is no separate communication unit 160, and the communication function is integrated within defibrillator 300. FIG. 3 does not show any support for external defibrillator 300, which may be carried by patient in a purse, on a belt, by a strap over the shoulder, and so on. Defibrillator 300 includes a user interface which, in this example, includes a screen 380. Screen 380 may be small because defibrillator 300 is made as small and lightweight as possible.

Wires 305 connect external defibrillator 300 to electrodes 304, 308, 309. Of those, electrodes 304, 308 are defibrillation electrodes, and electrodes 309 are ECG sensing electrodes.

Support structure 370 is configured to be worn by the ambulatory patient so as to maintain electrodes 304, 308, 309 on a body of the patient. Indeed, back defibrillation electrodes 308 are maintained in pockets 378. Of course, the inside of pockets 378 can be made with loose netting, so that electrodes 308 can contact the back of the patient, especially with the help of the conductive fluid that has been deployed. In addition, sensing electrodes 309 are maintained in positions that surround the patient's torso, for sensing ECG signals and/or the impedance of the patient.

In the example of FIG. 3, a peripheral device 340 is also provided. In this example, peripheral device 340 is tethered with defibrillator 300 via a cable 371. In this example, a peripheral UI output device of peripheral device 340 is peripheral screen 346.

Figure 4:
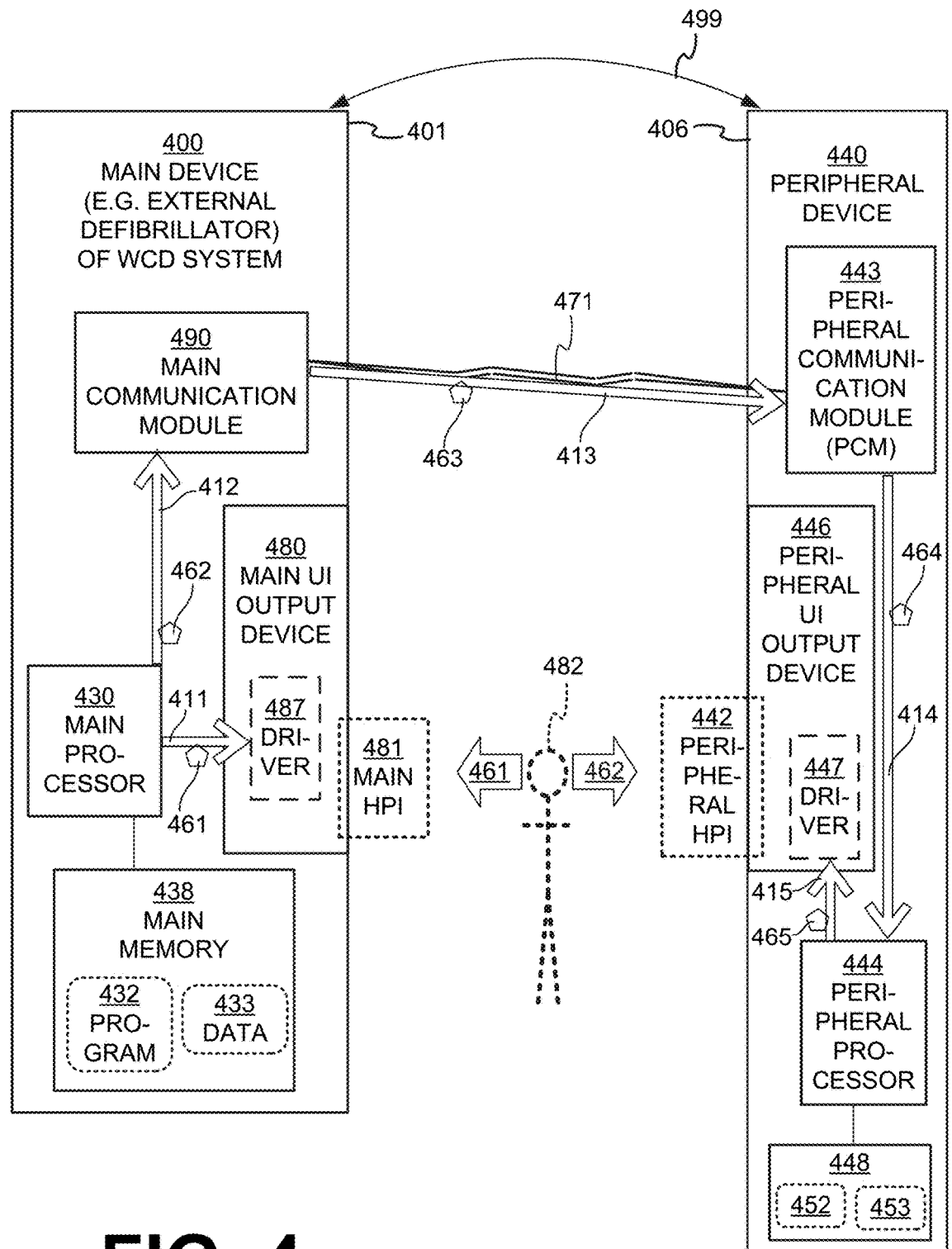
FIG. 4 is a composite diagram that includes block diagrams of a sample main device and a sample peripheral device made and operating according to embodiments.

FIG. 4 is a composite diagram that includes block diagrams of a sample main device 400 and a sample peripheral device 440 made and operating according to embodiments. Main device 400 is part of a WCD system made according to embodiments, and includes a main housing 401. In some embodiments, main device 400 is part of the external defibrillator which, for instance is the case if energy storage module 250 is located within main housing 401. In other embodiments, main device 400 could be analogous to communication unit 160 of FIG. 1, and be provided separately from the housing of the defibrillator unit.

In the example of FIG. 4, main device 400 includes a main processor 430, and a main memory 438 that stores data 433 and one or more programs 432. Moreover, main device 400 includes a main communications module 490, and a main user interface (UI) output device 480. Device 480 can be located at least partly within main housing 401, and include a driver 487 that can be a device driver.

In some embodiments, a main processor such as processor 430 is configured to receive an input about a condition. The condition can be about one of ambulatory patient 82, and of a component of the WCD system, of which examples are given later in this document. The intent is to communicate that condition to patient 82. The input about the condition may be received by any one of the sensors described in this document, or may be generated internally by a separate process of one of the processors of a WCD system, and so on.

In such embodiments, a main processor such as processor 430 can be configured to cause, responsive to the received input, a main UI output device such as device 480 to output a main human-perceptible indication (HPI) such as main HPI 481. The main HPI can be about the condition, as per examples are described later. Main UI output device 480 can be implemented in number of ways, for the appropriate main HPI. For example, the device 480 can include a main speaker configured to emit a sound, a main vibration device configured to generate a vibration, a main screen configured to display an image, and so on. The main screen can be a touchscreen.

In the particular example of FIG. 4, main processor 430 is configured to transmit, responsive to the received input, a main driving signal 461 to main UI output device 480 according to arrow 411. And, main UI output device 480 is configured to output main HPI 481 responsive to receiving main driving signal 461.

In such embodiments, a main processor such as processor 430 can be further configured to cause, responsive to the received input, a main communication module such as main communication module 490 to transmit an amplification signal. The amplification signal may encode a message about the condition.

In the particular example of FIG. 4, main processor 430 is configured to transmit, responsive to the received input, a main notification signal 462 to main communication module 490 according to arrow 412. And, main communication module 490 is configured to transmit amplification signal 463 responsive to receiving main notification signal 462.

In some embodiments of FIG. 4, peripheral device 440 is part of the WCD system of main device 400. In other embodiments, peripheral device 440 is a commercially available device that does not start as being part of the WCD system. In such embodiments, by loading an appropriate software application to peripheral device 440, main device 400 enables peripheral device 440 to amplify the message output by main device 400, as seen later in this document. And, in either type of embodiment, main device 400 can be considered in a combination 499 with peripheral device 440, with which it cooperates.

Peripheral device 440 includes a peripheral housing 406. Peripheral housing 406 is distinct from main housing 401. Peripheral device 440 also includes a peripheral communication module (PCM) 443. PCM 443 is located at least partly within peripheral housing 406.

In embodiments, a PCM such as PCM 443 is configured to receive the amplification signal with the encoded message, which is transmitted by a main communication module such as module 490. In the example of FIG. 4, communication module 490 transmits amplification signal 463 according to arrow 413 over comlink 471. Comlink 471 can be implemented in number of ways. For one example, comlink 471 can be as described for cable 371. For another example, comlink 471 can be wireless, such as was described for comlink 171. In such instances, the main UI output device includes an antenna, the PCM includes an antenna, and the amplification signal is transmitted and received wirelessly.

In some embodiments, the peripheral device also includes a peripheral UI output device, such as was described above for peripheral device 140. In the particular example of FIG. 4, peripheral device 440 also includes a peripheral UI output device 446. The peripheral UI output device can be configured, responsive to the PCM receiving the amplification signal with the encoded message, to output a peripheral HPI. The peripheral HPI can be about the condition, intended as a message to the user. In the particular example of FIG. 4, peripheral UI output device 446 cam output peripheral HPI 442.

In some embodiments, as also in the particular example of FIG. 4, peripheral device 440 further includes a peripheral processor 444, and also a peripheral memory 448 that stores data 453 and one or more programs 452. Processor 444 can be configured, responsive to PCM 443 receiving amplification signal 463, to decode the message about the condition that is encoded in the amplification signal, and drive peripheral UI output device 446 to output peripheral HPI 442.

In the particular example of FIG. 4, peripheral UI output device 446 has a driver 447 that can be a device driver. PCM 443 is further configured to transmit, responsive to receiving amplification signal 463, a peripheral notification signal 464 to peripheral processor 444 according to arrow 414. And, peripheral processor 444 can be further configured to transmit, responsive to receiving peripheral notification signal 464, a peripheral driving signal 465 to peripheral UI output device 446, according to arrow 415. Then, peripheral UI output device 446 is configured to output peripheral HPI 442 responsive to receiving peripheral driving signal 415.

In FIG. 4, a patient 482 is shown, who can be the same a patient 82 and wearer 282. Patient 482 has a first option 461 to experience main HPI 481 about the condition. In addition, thanks to embodiments, patient 482 has a second option 462 to experience peripheral HPI 442 about the condition. As mentioned elsewhere in this document, peripheral HPI 442 may be amplified compared to main HPI 481, and therefore easier to experience, understand, and even explore.

It will be understood, of course, that peripheral HPI 442 can be output concurrently with main HPI 481, or not. In fact, peripheral HPI 442 may depend on peripheral device 440 being procured, accessed, and so on.

There are a number of conditions for each of which main HPI 481 and peripheral HPI 442 may be output according to embodiments. Examples are now described.

In some embodiments, the WCD system further includes a sensor. A number of sensors have already been described. In such embodiments, the sensor can be configured to monitor a patient parameter of ambulatory patient 82, and the condition includes a value of the patient parameter. In other embodiments, the sensor can be configured to monitor an operational parameter of the WCD system, and the condition includes a value of the operational parameter, or that such a value is beyond a threshold. In some embodiments, the WCD system includes a battery, and a charge monitor configured to monitor a state of charge of the battery. In such embodiments, the condition includes a value for the state of charge.

In some embodiments, the WCD system further includes a wear monitor. The wear monitor can be configured to determine whether or not the support structure is worn by the ambulatory patient in a certain way, and to output a wear confirmation responsive to determining that the support structure is indeed worn by the ambulatory patient in the certain way. In such embodiments, the condition can include an indication of the wear confirmation. Examples of wear monitors are given in commonly owned U.S. Pat. No. 9,757,576, titled "RELIABLE READINESS INDICATION FOR A WEARABLE DEFIBRILLATOR".

Still referring to FIG. 4, main HPI 481 about a condition may be of different types, e.g. visual such as an image, auditory such as a sound, or tactile such as a vibration. Similarly, the peripheral HPI 442 about the condition may be of different types, e.g. visual such as an image, auditory such as a sound, or tactile such as a vibration. For notifying patient 482 about a single condition, peripheral HPI 442 may or may not be of the same type as main HPI 481. Of course, both main HPI 481 and peripheral HPI 442 may be images. Examples are now described.

Figure 5:
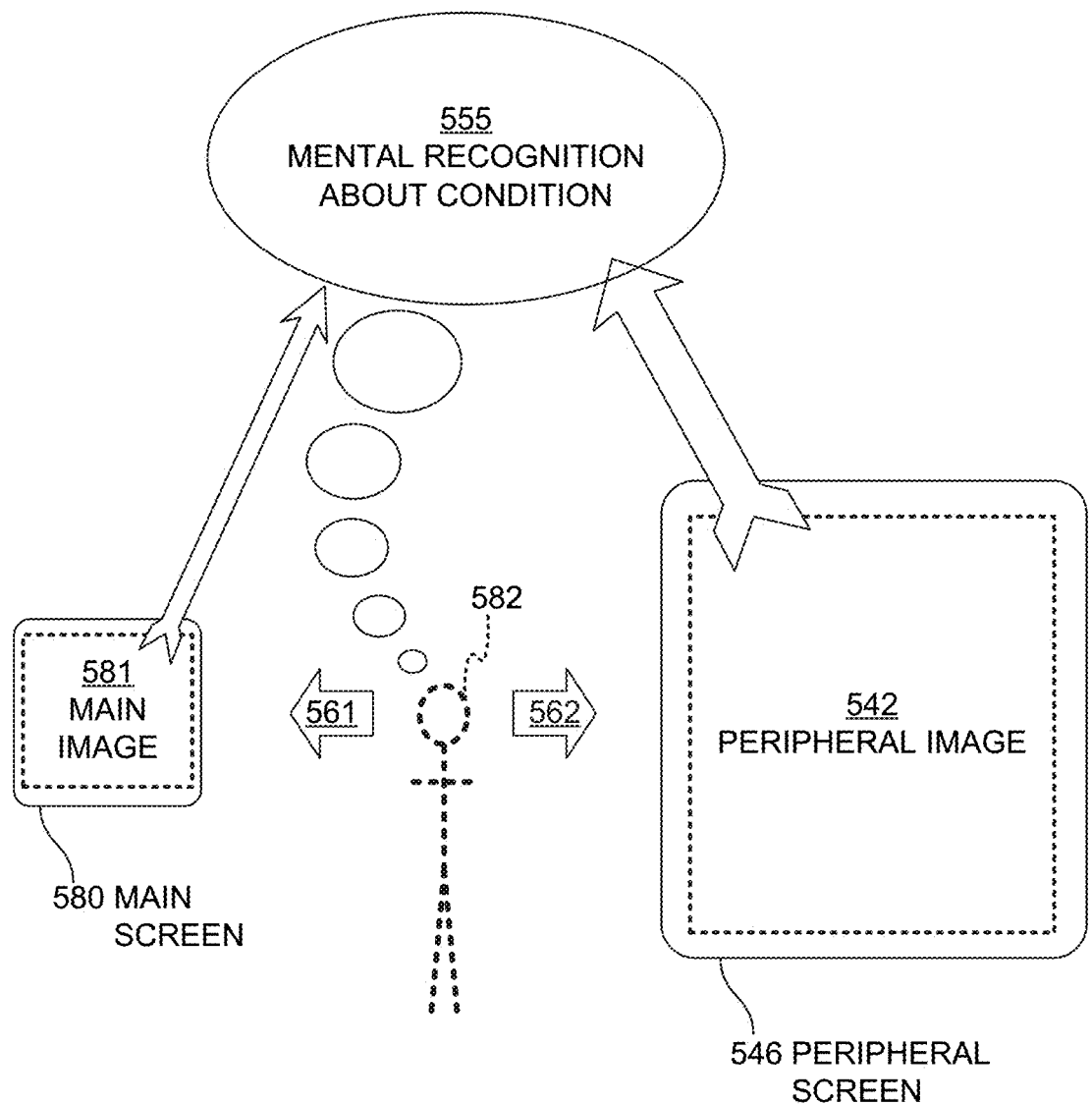
FIG. 5 is a diagram of sample components according to embodiments, where the main UI output device includes a main screen that displays a main image about a condition to be conveyed to a patient, and the peripheral UI output device includes a peripheral screen that displays a peripheral image about the condition.

FIG. 5 is a diagram of sample components according to embodiments. A main UI output device includes a main screen 580. Screen 580 displays a main image 581 about a condition, for a patient 582 to reach a mental recognition 555. In addition, a peripheral UI output device includes a peripheral screen 546. Screen 546 displays a peripheral image 542 about the condition. Peripheral image 542 may repeat, amplify or augment main image 581, to further facilitate patient 582 reach mental recognition 555. Patient 582 has the option to look in direction 561 towards main image 581, or in direction 562 towards peripheral image 542. In some embodiments, wearer 585 need to look only in direction 562, at a single location, to glean the required information from all communicating components of the WCD system.

Examples of such images are now described.

Figure 6:
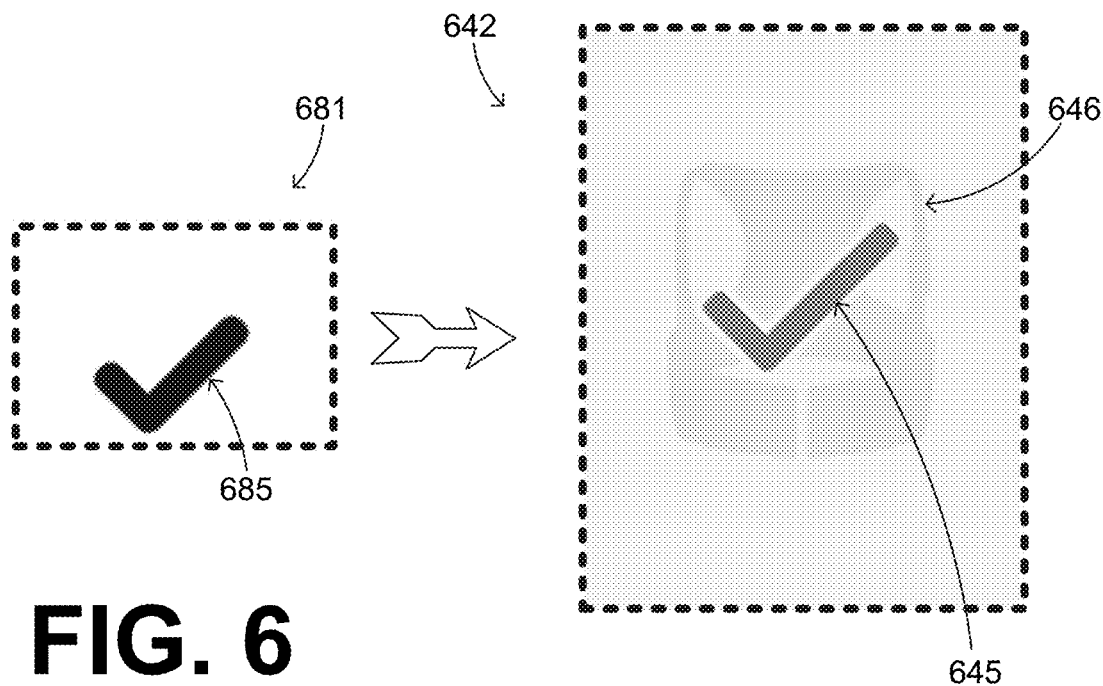
FIG. 6 is a diagram of a sample main image, and a corresponding sample peripheral image that repeats the entire main image, according to embodiments.

FIG. 6 is a diagram of a sample main image 681, and a corresponding sample peripheral image 642. Main image 681 shows a checkmark 685. Peripheral image 642 includes the entire main image, by showing a checkmark 645. It will be recognized that checkmark 645, as would be displayed on the peripheral screen, has at least 24% larger area than checkmark 685 as displayed on the main screen, for easier viewing.

In addition, peripheral image 642 includes a second image 646 that is not included in the main image. In this particular case, second image 646 is of the vest 370, which enhances mental recognition 555 that checkmarks 685, 645 inform that vest 370 is worn in the appropriate way.

Figure 7:
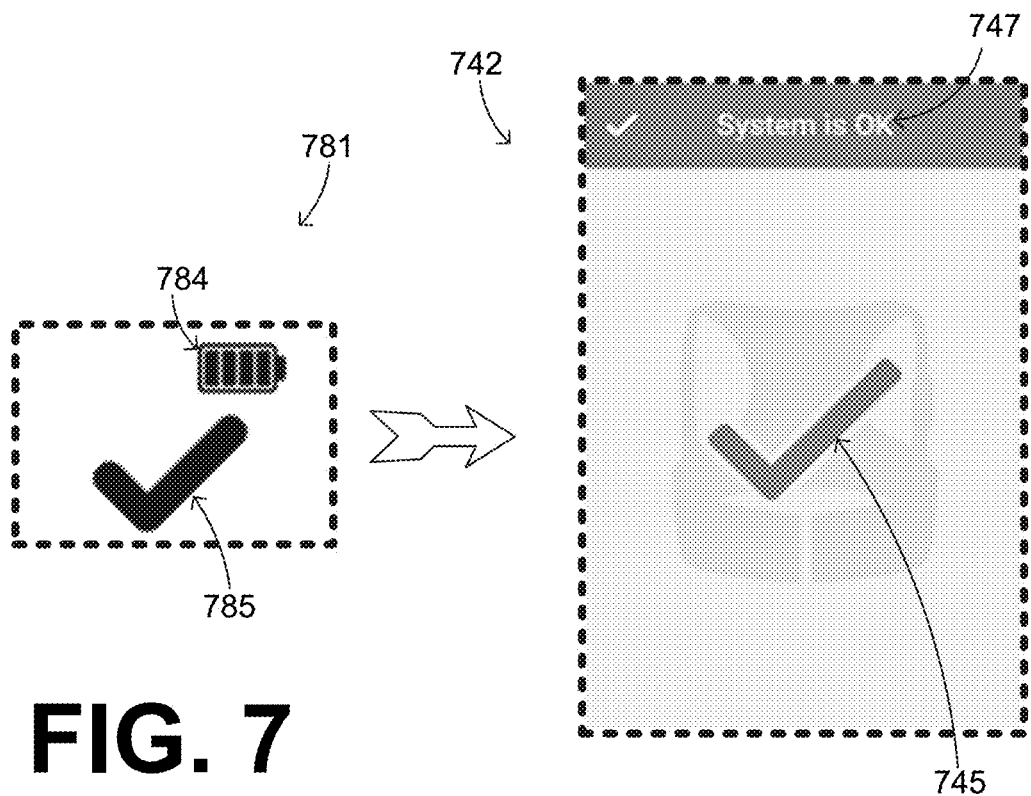
FIG. 7 is a diagram of a sample main image, and a corresponding sample peripheral image that repeats an aspect of the main image plus provides text, according to embodiments.

FIG. 7 is a diagram of a sample main image 781, and a corresponding sample peripheral image 742. Main image 781 shows a checkmark 785 and an icon 784 for the battery charge status. Peripheral image 742 includes a checkmark 745, which is only an aspect of main image 781, but does not repeat the entire main image—for icon 784 is not repeated.

In addition, peripheral image 742 includes text 747 that is not included in main image 781. In this particular case, text 747 enhances mental recognition 555 that the whole WCD system is OK.

It will be recognized that peripheral images 642, 742 can easily be displayed in a device that is the size of a mobile phone. As such, they may be larger than main screen 580, convey more information, be easier to read, and so on.

In some embodiments, even more information is presented by the peripheral image. In such embodiments, the peripheral image can have multiple portions, such as a first portion and a second portion, and so on. In such embodiments, the peripheral UI output device includes a screen configured to initially display the first portion but not the second portion, and then to display the second portion without the first portion, and so on. Displaying the successive portions can be performed in a number of ways. One such way is by a short video. Another such way is for the peripheral UI output device to include a touchscreen. The touchscreen can be configured to display the second portion responsive to the touchscreen being touched, for example by swiping. Another example is now described.

Figure 8:
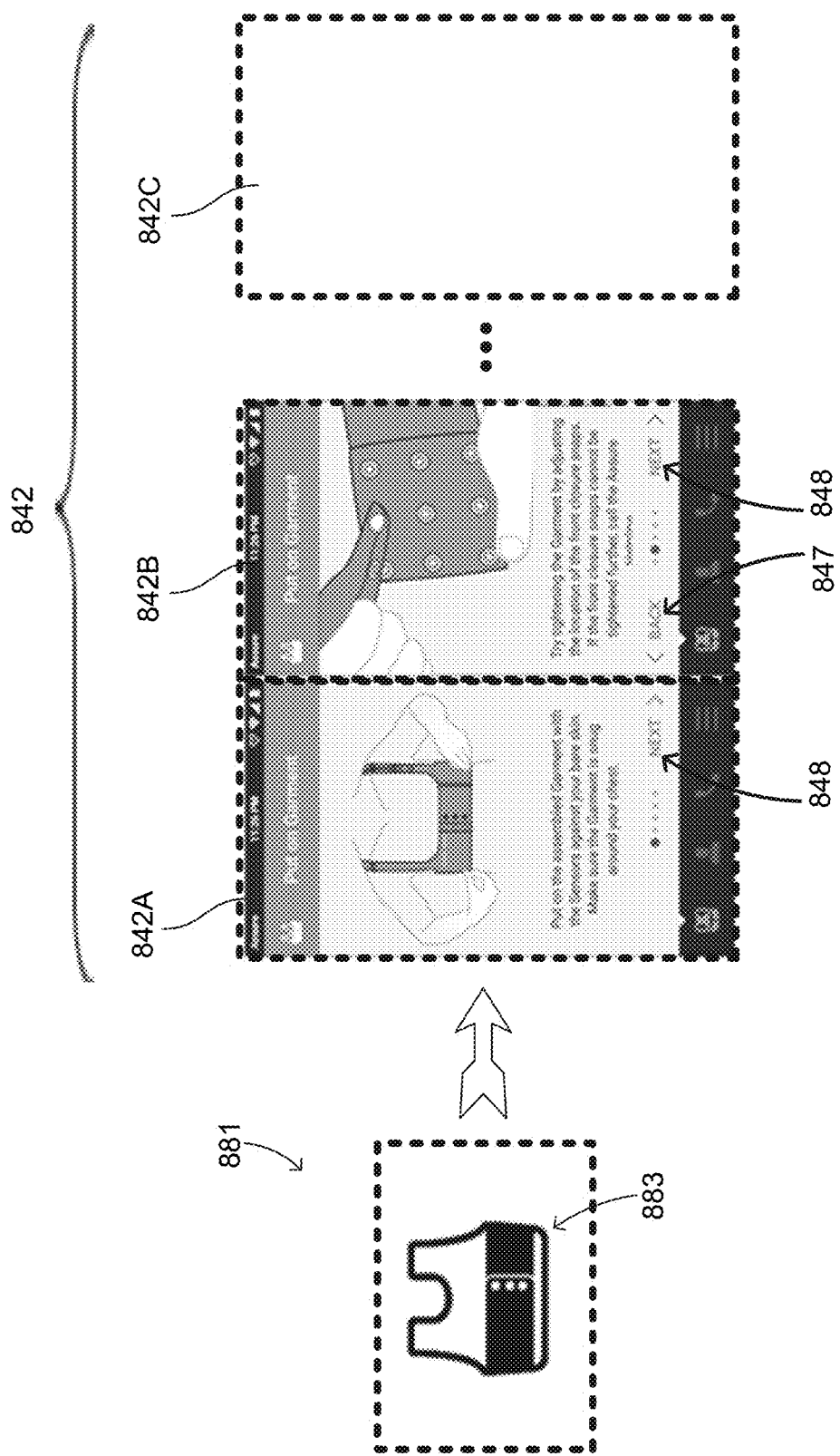
FIG. 8 is a diagram of a sample main image, and a corresponding sample peripheral image having multiple portions that can be viewed in succession by links, according to embodiments.

FIG. 8 is a diagram of a sample main image 881, and a corresponding sample peripheral image 842. Peripheral image 842 has multiple portions 842A, 842B, . . . 842C. Image portions 842A, 842B, include links 847, 848, which point to the previous or the next image portion. The touchscreen can be configured to display the next portion responsive to the touchscreen being touched at the appropriate link.

In some embodiments, even more information is presented by the peripheral image, when peripheral screen 546 is of a larger device, such as a tablet computer. An example is now described.

Figure 9:
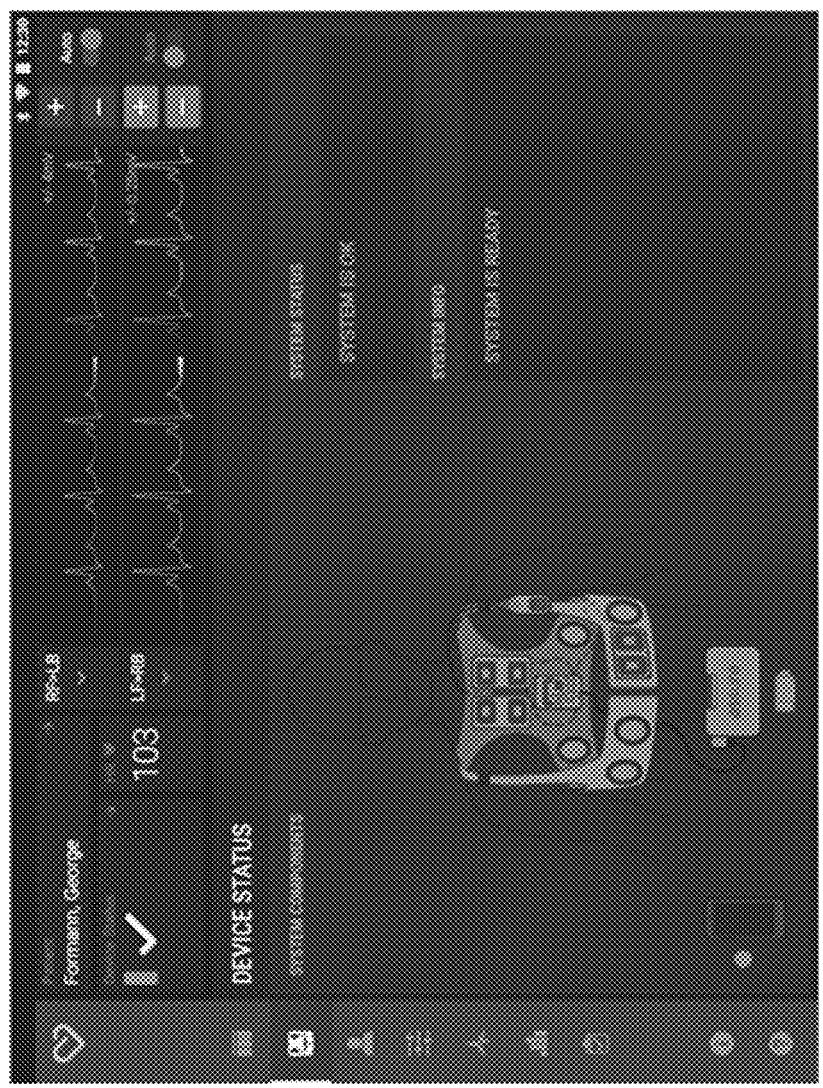
FIG. 9 is a diagram of a sample main image, and a corresponding sample peripheral image that is displayed in a peripheral device of a larger size such as a tablet, according to embodiments.
Figure 9:
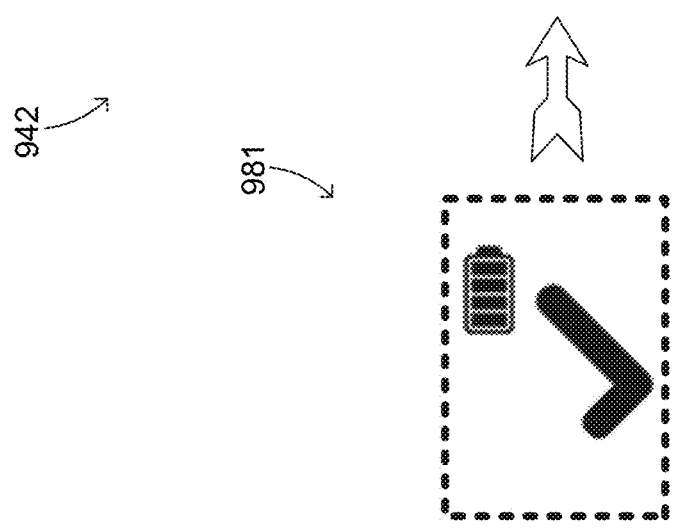

FIG. 9 is a diagram of a sample main image 981, and a corresponding sample peripheral image 942. It will be recognized that, in this example, main image 981 is identical to main image 781 of FIG. 7 In addition, peripheral image 942 is displayed in a tablet and includes much more information, all in a single image portion.

It will be appreciated that embodiments give patient 82, 482, 582 the option to receive messages by the WCD system via peripheral device 140, 440, as opposed to via communication unit 160 or main device 400. Using device 140 will attract less attention in public places where others may be watching, than using communication unit 160. In addition, using device 140 will be less distracting to people familiar with patient 82, and the fact that this patient needs to be attending to their WCD system. As such, patient 82 will have one less deterrent from exhibiting good compliance in actually wearing their WCD system daily.

A further advantage of embodiments is that messages to patient 82, 482, 582 from peripheral device 140 may be amplified, compared to those from communication unit 160. By amplified, it is meant that they can be larger in area for viewing, contain more explanation, and so on.

Embodiments may overcome problems where users have difficulty correctly interpreting and/or perceiving the main UI output device the WCD system, for example in cases where: a) the main UI output device has a small screen so it is difficult for users to see the content of the screen, b) the main UI output device is not loud enough for users, or c) the main UI output device does not output enough vibratory feedback for users. In embodiments peripheral HPIs 442, 1042 can be larger, louder, and vibrate stronger.

Embodiments may further solve the problem where the user cannot understand an icon presented on the display of a medical device. In embodiments peripheral HPIs 442, 1042 contain more information, such as additional descriptive information about the state of the device, tips about the device's current condition, and/or directions for the next step in addressing the medical device's current condition.

Embodiments may further overcome problems where the main UI output device of the WCD system is too obtrusive, for example it is too loud. In embodiments peripheral HPIs 442, 1042 can permit the user to put the medical device in a silent mode and respond to a peripheral HPI that allows for more concealed and discreet use. Indeed, a peripheral device allows a patient to keep the primary device "hidden" out of sight while remaining informed of the primary device's condition.

Embodiments may additionally solve the problem where the user is not near the medical device to correctly interpret and/or perceive the main HPI. For example, a bed-bound patient needs to view the display of a device, perhaps a stationary device, but the device could be too far away to correctly interpret the display contents. It is easier, however, for them to handle the peripheral device.

Embodiments may furthermore improves the setup process of a medical device by allowing a person that is setting up the primary device to see what the patient sees, without obstructing the patient's view of the primary device or interfering with the patient's use of the primary device.

The devices and/or systems mentioned in this document may perform functions, processes, acts, operations, actions and/or methods. These functions, processes, acts, operations, actions and/or methods may be implemented by one or more devices that include logic circuitry. A single such device can be alternately called a computer, and so on. It may be a standalone device or computer, such as a general-purpose computer, or part of a device that has and/or can perform one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description may include flowcharts, display images, algorithms, and symbolic representations of program operations within at least one computer readable medium. An economy may be achieved in that a single set of flowcharts can be used to describe both programs, and also methods. So, while flowcharts describe methods in terms of boxes, they may also concurrently describe programs.

Methods are now described.

Figure 10:
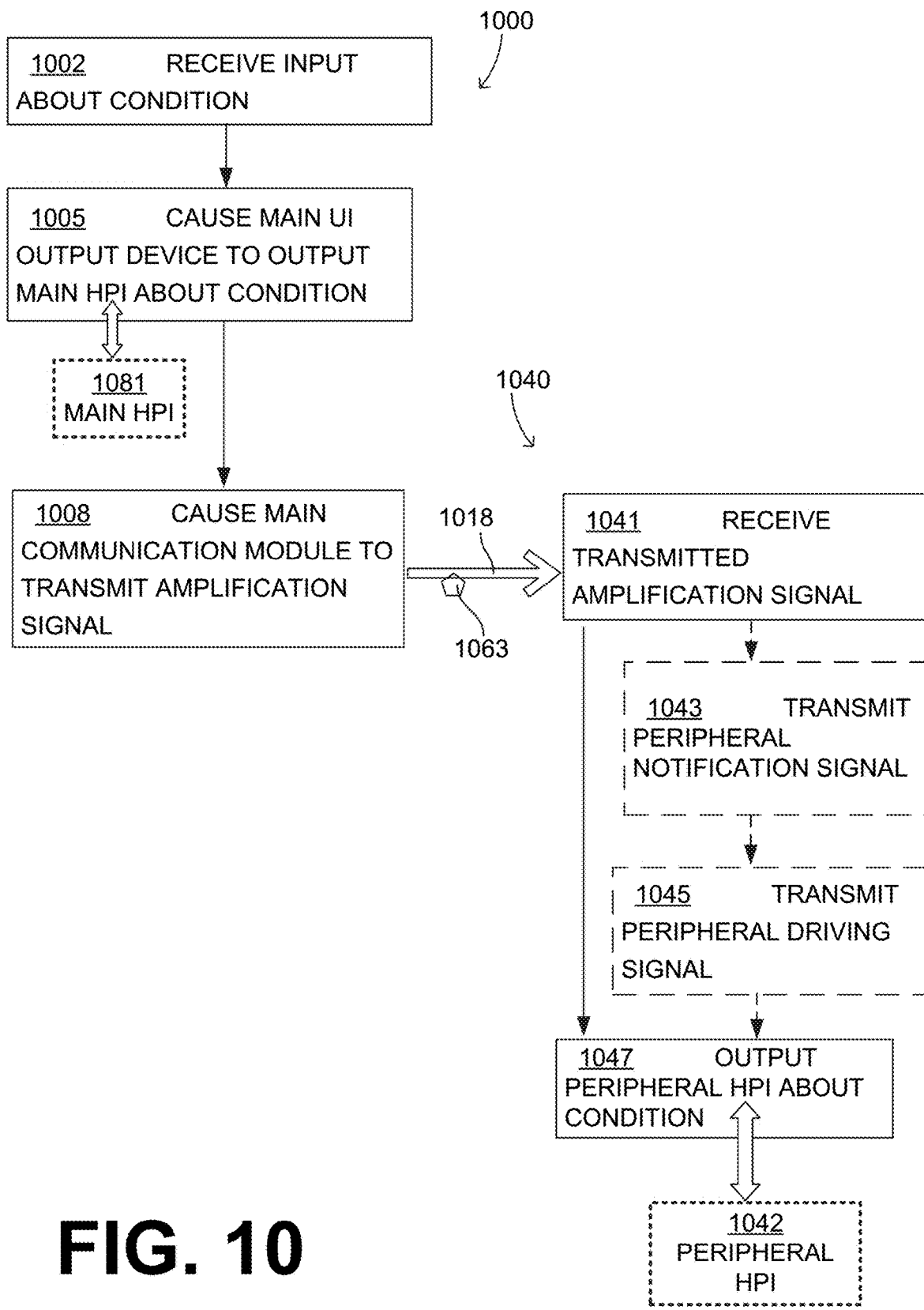
FIG. 10 shows flowchart portions for illustrating sample methods according to embodiments, the flowchart further annotated with icons of elements that can be related to individual operations of the flowchart portions.

FIG. 10 shows flowchart portions 1000, 1040 for describing methods according to embodiments. The methods of flowchart portion 1000 may be performed by a device of a WCD system such as main device 400. The methods of flowchart portion 1040 may be performed by a peripheral device such as peripheral device 440. Flowchart portions 1000, 1040 include operations that are linked by arrows. Icons of elements are further added for purposes of illustration. Arrow 1018 may or may not form part of a flowchart that combines portions 1000, 1040 into a single flowchart, for example depending on whether or not a peripheral device is part of a WCD system.

According to an operation 1002, an input about a condition may be received by a main processor.

According to another operation 1005, a main UI output device can be caused to output a main human-perceptible indication (HPI) 1081. Main HPI 1081 can be about the condition, similarly with main HPI 481. Operation 1005 may be performed responsive to the input received at operation 1002.

According to another operation 1008, a main communication module can be caused to transmit an amplification signal 1063. Amplification signal 1063 may encode a message about the condition, similarly with amplification signal 463.

According to another operation 1041, amplification signal 1063 with the encoded message that was transmitted at operation 1008 may be received by a peripheral communication module (PCM).

According to another operation 1047, a peripheral UI output device may output a peripheral HPI 1042, responsive to the PCM receiving amplification signal 1063 with the encoded message at operation 1041. Peripheral HPI 1042 may be about the condition, similarly with peripheral HPI 442.

In some embodiments, according to another, optional operation 1043, a peripheral notification signal is transmitted by the PCM to a peripheral processor responsive to receiving the amplification signal with the encoded message. Then, according to another, optional operation 1045, a peripheral driving signal is transmitted by the peripheral processor to the peripheral UI output device, responsive to the peripheral processor receiving the peripheral notification signal with the encoded message. In these embodiments, operation 1047 is performed by the peripheral UI output device responsive to the peripheral driving signal.

In the methods described above, each operation can be performed as an affirmative act or operation of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description.

Some technologies or techniques described in this document may be known. Even then, however, it does not necessarily follow that it is known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to", "adapted to" and/or "configured to" denote one or more actual states of construction, adaptation and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Parent patent applications: Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

Reference numerals: In this description a single reference numeral may be used consistently to denote a single item, aspect, component, or process. Moreover, a further effort may have been made in the preparation of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. The claims also include elements, features and acts or operations that are equivalent to what is explicitly mentioned. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A wearable cardioverter defibrillator (WCD) system configured to be worn by an ambulatory patient, comprising:
   an electrode;
   a support structure configured to be worn by the ambulatory patient so as to maintain the electrode on a body of the ambulatory patient;

an energy storage module configured to store an electrical charge, and to discharge at least some of the stored electrical charge via the electrode through the ambulatory patient;
a main housing;
a main user interface (UI) output device located at least partly within the main housing;
a main communication module;
a main processor configured to:
receive an input about a condition, the condition being about one of the ambulatory patient and a component of the WCD system,
cause, responsive to the received input, the main UI output device to output a main human-perceptible indication (HPI), the main HPI being about the condition, and
cause, responsive to the received input, the main communication module to transmit an amplification signal, the amplification signal encoding and amplifying a message about the condition; and
a peripheral device that is configured to be carried by the ambulatory patient, the peripheral device comprising:
a peripheral housing distinct from the main housing;
a peripheral communication module (PCM) located at least partly within the peripheral housing, the PCM configured to receive the transmitted amplification signal with the encoded and amplified message; and
a peripheral UI output device configured, responsive to the PCM receiving the amplification signal with the encoded and amplified message, to output a peripheral HPI, the peripheral HPI being about the condition.

2. The WCD system of claim 1, in which
the energy storage module is located within the main housing.

3. The WCD system of claim 1, in which
the main UI output device includes an antenna,
the PCM includes an antenna, and
the amplification signal is transmitted and received wirelessly via the antenna of the main UI output device and via the antenna of the PCM.

4. The WCD system of claim 1, in which
the peripheral device further comprises:
a peripheral processor configured, responsive to the PCM receiving the amplification signal, to decode the encoded message and drive the peripheral UI output device to output the peripheral HPI.

5. The WCD system of claim 1, in which
the peripheral HPI is output concurrently with the main HPI.

6. The WCD system of claim 1, further comprising:
a sensor configured to monitor a patient parameter of the ambulatory patient, and
in which the condition includes a value of the patient parameter.

7. The WCD system of claim 1, further comprising:
a sensor configured to monitor an operational parameter of the WCD system, and
in which the condition includes a value of the operational parameter.

8. The WCD system of claim 1, further comprising:
a sensor configured to monitor an operational parameter of the WCD system, and
in which the condition includes that a value of the operational parameter is beyond a threshold.

9. The WCD system of claim 1, further comprising:
a battery; and
a charge monitor configured to monitor a state of charge of the battery, and
in which the condition includes a value for the state of charge.

10. The WCD system of claim 1, further comprising:
a wear monitor configured to determine whether or not the support structure is worn by the ambulatory patient in a certain way, and to output a wear confirmation responsive to determining that the support structure is worn by the ambulatory patient in the certain way, and
in which the condition includes an indication of the wear confirmation.

11. The WCD system of claim 1, in which
the main HPI includes a sound,
the main UI output device includes a main speaker configured to emit the sound,
the peripheral HPI includes an image, and
the peripheral UI output device includes a peripheral screen configured to display the image.

12. The WCD system of claim 1, in which
the main HPI includes a vibration,
the main UI output device includes a main vibration device configured to emit the vibration,
the peripheral HPI includes an image, and
the peripheral UI output device includes a peripheral screen configured to display the image.

13. The WCD system of claim 1, in which
the peripheral HPI includes a sound, and
the peripheral UI output device includes a peripheral speaker configured to emit the sound.

14. The WCD system of claim 1, in which
the peripheral HPI includes a vibration, and
the peripheral UI output device includes a peripheral vibration device configured to generate the vibration.

15. The WCD system of claim 1, in which
the main HPI includes a main image,
the main UI output device includes a main screen configured to display the main image,
the peripheral HPI includes a peripheral image, and
the peripheral UI output device includes a peripheral screen configured to display the peripheral image.

16. The WCD system of claim 15, in which
the peripheral image that includes the entire main image.

17. The WCD system of claim 15, in which
the peripheral image includes a second image that is not included in the main image.

18. The WCD system of claim 15, in which
the peripheral image includes an aspect of the main image, and
the aspect of the main image as displayed on the peripheral screen has at least 24% larger area than as displayed on the main screen.

19. The WCD system of claim 15, in which
the peripheral image includes an aspect of the main image.

20. The WCD system of claim 15, in which
the peripheral image includes text that is not included in the main image.

21. The WCD system of claim 15, in which
the peripheral image has a first portion and a second portion, and
the peripheral UI output device includes a screen configured to initially display the first portion but not the second portion, and then to display the second portion.

22. The WCD system of claim 21, in which
the peripheral UI output device includes a touchscreen, the touchscreen configured to display the second portion responsive to the touchscreen being touched.

23. The WCD system of claim 21, in which
the first portion includes a link, and
the peripheral UI output device includes a touchscreen, the touchscreen configured to display the second portion responsive to the touchscreen being touched at the link.

24. Non-transitory computer-readable storage media storing programs which, when executed by at least a main processor and a peripheral processor of a wearable cardioverter defibrillator (WCD) system that is configured to be worn by an ambulatory patient, the WCD system including an electrode, a support structure configured to be worn by the ambulatory patient so as to maintain the electrode on a body of the ambulatory patient, an energy storage module configured to store an electrical charge, and to discharge at least some of the stored electrical charge via the electrode through the ambulatory patient, a main housing, a main user interface (UI) output device located at least partly within the main housing, a main communication module, the main processor, and a peripheral device that is configured to be carried by the ambulatory patient, the peripheral device including a peripheral housing distinct from the main housing, the peripheral processor, a peripheral communication module (PCM) located at least partly within the peripheral housing, and a peripheral UI output device, these programs result in operations comprising:
    receiving, by the main processor, an input about a condition, the condition being about one of the ambulatory patient and a component of the WCD system;
    causing, responsive to the received input, the main UI output device to output a main human-perceptible indication (HPI), the main HPI being about the condition;
    causing, responsive to the received input, the main communication module to transmit an amplification signal, the amplification signal encoding and amplifying a message about the condition;
    receiving, by the PCM, the transmitted amplification signal with the encoded and amplified message;
    transmitting, by the PCM, a peripheral notification signal to the peripheral processor responsive to receiving the amplification signal with the encoded and amplified message;
    transmitting, by the peripheral processor, a peripheral driving signal to the peripheral UI output device responsive to the peripheral processor receiving the peripheral notification signal with the encoded and amplified message; and
    outputting, by the peripheral UI output device, a peripheral HPI responsive to the peripheral driving signal, the peripheral HPI being about the condition.

25. A method for a wearable cardioverter defibrillator (WCD) system that is configured to be worn by an ambulatory patient, the WCD system including an electrode, a support structure configured to be worn by the ambulatory patient so as to maintain the electrode on a body of the ambulatory patient, an energy storage module configured to store an electrical charge, and to discharge at least some of the stored electrical charge via the electrode through the ambulatory patient, a main housing, a main user interface (UI) output device located at least partly within the main housing, a main communication module, a main processor, and a peripheral device that is configured to be carried by the ambulatory patient, the peripheral device including a peripheral housing distinct from the main housing, a peripheral communication module (PCM) located at least partly within the peripheral housing, and a peripheral UI output device, the method comprising:
    receiving, by the main processor, an input about a condition, the condition being about one of the ambulatory patient and a component of the WCD system;
    causing, responsive to the received input, the main UI output device to output a main human-perceptible indication (HPI), the main HPI being about the condition;
    causing, responsive to the received input, the main communication module to transmit an amplification signal, the amplification signal encoding and amplifying a message about the condition;
    receiving, by the PCM, the transmitted amplification signal with the encoded and amplified message; and
    outputting, by the peripheral UI output device, a peripheral HPI responsive to the PCM receiving the amplification signal with the encoded and amplified message, the peripheral HPI being about the condition.

* * * * *